United States Patent
Kabashima

(10) Patent No.: US 9,434,199 B2
(45) Date of Patent: Sep. 6, 2016

(54) THERMAL RECORDING MATERIAL

(71) Applicant: Fine Ace Corporation, Tokyo (JP)

(72) Inventor: Kazuo Kabashima, Tokyo (JP)

(73) Assignee: Fine Ace Corporation, Tokyo (JP)

(*) Notice: Subject to any disclaimer, the term of this patent is extended or adjusted under 35 U.S.C. 154(b) by 47 days.

(21) Appl. No.: 14/386,657

(22) PCT Filed: Mar. 19, 2013

(86) PCT No.: PCT/JP2013/057755
§ 371 (c)(1),
(2) Date: Sep. 19, 2014

(87) PCT Pub. No.: WO2013/141224
PCT Pub. Date: Sep. 26, 2013

(65) Prior Publication Data
US 2015/0051070 A1 Feb. 19, 2015

(30) Foreign Application Priority Data
Mar. 21, 2012 (JP) ................. 2012-064226

(51) Int. Cl.
*B41M 5/333* (2006.01)
*B41M 5/337* (2006.01)
*C07C 315/04* (2006.01)
*C07C 317/22* (2006.01)

(52) U.S. Cl.
CPC ......... *B41M 5/3336* (2013.01); *B41M 5/3375* (2013.01); *C07C 315/04* (2013.01); *C07C 317/22* (2013.01); *B41M 2205/04* (2013.01)

(58) Field of Classification Search
CPC .. B41M 5/333; B41M 5/3336; B41M 5/337; B41M 2205/04; C07C 315/04; C07C 317/22

USPC .................................................. 503/209, 216
See application file for complete search history.

(56) References Cited

FOREIGN PATENT DOCUMENTS

| | | |
|---|---|---|
| EP | 0616897 A2 | 9/1994 |
| EP | 0618082 A1 | 10/1994 |
| GB | 2476147 A | 6/2011 |
| JP | 5-92665 A | 4/1993 |
| JP | 2001/080218 A | 3/2001 |

(Continued)

OTHER PUBLICATIONS

International Search Report for corresponding International Application No. PCT/JP2013/057755, mailed Jun. 18, 2013 (2 pages).

(Continued)

*Primary Examiner* — Bruce H Hess
(74) *Attorney, Agent, or Firm* — Osha Liang LLP

(57) ABSTRACT

A thermal recording material having both of excellent coloring property and storage stability with a low cost is provided. The thermal recording material contains a leuco dye and a developer in a coloring layer, and the developer contains 2,4'-dihydroxydiphenylsulfone and 4,4'-dihydroxydiphenylsulfone with a specific ratio, and the above-mentioned two kinds of the dihydroxydiphenylsulfones are made a material obtained by sequentially undergoing a separating step for heightening the weight ratio of a 2,4' material from a dichlorodiphenylsulfone mixture containing the 2,4' material and a 4,4' material, a reaction step of hydrolyzing the mixture to obtain a dihydroxydiphenylsulfone mixture, and a post-treatment step of subjecting to decolorization and purification.

17 Claims, 2 Drawing Sheets

(56) References Cited

FOREIGN PATENT DOCUMENTS

| | | |
|---|---|---|
| JP | 2001-260544 A | 9/2001 |
| JP | 2002-120462 A | 4/2002 |
| JP | 2002-144742 A | 5/2002 |
| JP | 2003-246152 A | 9/2003 |
| JP | 2004-042401 A | 2/2004 |
| JP | 2004-114366 A | 4/2004 |
| JP | 2004-182668 A | 7/2004 |
| JP | 2004-256421 A | 9/2004 |
| JP | 2005-41151 A | 2/2005 |
| JP | 3739282 B2 | 1/2006 |
| JP | 3836868 B2 | 8/2006 |
| JP | 3913820 B2 | 2/2007 |
| WO | 00/14058 A1 | 3/2000 |

OTHER PUBLICATIONS

Extended European Search Report issued in corresponding European Application No. 13764169.2 dated Sep. 24, 2015 (6 pages).

THERMAL RECORDING MATERIAL

TECHNICAL FIELD

The present invention relates to a thermal recording material used in a facsimile machine, a printer, and so on, more specifically to a thermal recording material improved in coloring property and image stability with a low cost.

BACKGROUND ART

In recent years, a thermal recording system in which recording is carried out by heat energy is employed in many cases of various kinds of information appliances such as a facsimile machine, a printer, a recording equipment, and so on. The thermal recording material used in the thermal recording system has many excellent characteristics that a degree of whiteness is high, appearance or touch feeling is close to plain paper, recording suitability such as thermal coloring sensitivity and so on is good, and so on. In particular, a material which uses a colorless or pale colored electron donating dye precursor (in particular, a leuco dye) as a coloring agent and uses an acidic developer such as a phenolic compound has a characteristic that reactivity of the dye precursor which is an electron donating compound is high. There is an advantage that a colored image with high density can be obtained instantaneously when the dye precursor is contacted with the developer which is an electron accepting compound. On the other hand, it has drawbacks of poor storage stability of the recording that the obtained colored image is inferior in chemical resistance, so that the recording is likely disappeared by contacting with a plasticizer contained in a plastic sheet or an eraser or a chemical contained in foods or cosmetics, or the recording part is poor in light resistance, so that the recording is faded or disappeared by sunlight exposure with a relatively short period of time, and so on.

Thus, it has been proposed to use a mixture of 2,4'-dihydroxydiphenylsulfone and 4,4'-dihydroxydiphenylsulfone with various weight ratio as a developer which can relatively improve storage stability of recording (for example, see Patent Documents 4 and 5). Among these, 2,4'-dihydroxydiphenylsulfone has excellent basic properties as a thermal recording material, such as thermal coloring sensitivity, a degree of whiteness, and so on, so that there are disclosed inventions that the weight ratio of 2,4'-dihydroxydiphenylsulfone is heightened to be used for a thermal recording material (for example, see Patent Documents 1 and 6). However, 2,4'-dihydroxydiphenylsulfone is relatively inferior in recording stability, and production thereof is relatively difficult, and it has low production with high manufacturing cost. On the other hand, 4,4'-dihydroxydiphenylsulfone is relatively low in properties as a thermal recording material but its recording stability is good. In addition, it has conventionally been used as a starting material of polysulfone and so on, so that production thereof is relatively easy and it has been mass-produced with low manufacturing cost. By this reason, there have been disclosed inventions that a weight ratio of 4,4'-dihydroxydiphenylsulfone is heightened to be used for a thermal recording material (for example, see Patent Documents 2 and 3).

These 2,4'-dihydroxydiphenylsulfone and 4,4'-dihydroxydiphenylsulfone used in the thermal recording material have heretofore been manufactured as a mixture of isomers, by the manufacturing method in which one step reaction process is carried out by reacting a sulfonating agent, phenolsulfonic acid or sulfuric acid, and so on, with phenol. An original object of this manufacturing method is to manufacture the 4,4'-dihydroxydiphenylsulfone which is a starting material for a polysulfone and so on. According to this manufacturing method, the 4,4'-dihydroxydiphenylsulfone is formed with a weight ratio of, for example, 80 to 99.9%, and 2,4'-dihydroxydiphenylsulfone which is a byproduct is formed with a weight ratio of, for example, 0.1 to 20%. For manufacturing efficiently the 4,4'-dihydroxydiphenylsulfone which is the original objective material of this manufacturing method, it is usual to optimize the settings of the respective conditions of the reaction and so on, so that the weight ratio of the 2,4'-dihydroxydiphenylsulfone which is a byproduct becomes as small as possible.

However, in the case of the 2,4'-dihydroxydiphenylsulfone with larger weight ratio to use for the purpose of improving various properties of the thermal recording material, it is necessary to undergo the procedure that the 2,4'-dihydroxydiphenylsulfone or the 4,4'-dihydroxydiphenylsulfone is separated from the dihydroxydiphenylsulfone mixture formed by the above-mentioned manufacturing method, and then, the separated compound is added and mixed and so on, so that the resulting mixture has an objective weight ratio. This manufacturing process is shown in FIG. 2. The dihydroxydiphenylsulfone mixture thus manufactured has heretofore been used for a thermal recording material.

However, the 2,4'-dihydroxydiphenylsulfone and the 4,4'-dihydroxydiphenylsulfone have properties that solubilities thereof to a solvent for separation from each other are very close. Therefore, it is necessary for each purity improvement to undergo complex separating steps such that a pH adjustment and so on is carried out and a separating step is repeated. In order to obtain the 2,4'-dihydroxydiphenylsulfone with a high concentration, particularly in the usual case where the reaction conditions are previously so set that the formation ratio at the reaction of the 2,4'-dihydroxydiphenylsulfone becomes as small as possible, it is necessary to carry out the procedure to increase the concentration by using the mixture having the weight ratio only 0.1 to 0.2% for example. This procedure requires significant labor and time, whereby it causes high manufacturing cost of a thermal recording material which uses the 2,4'-dihydroxydiphenylsulfone with a high weight ratio.

Also, it has been known that in this manufacturing method, phenyl phenol-sulfonate or trihydroxytriphenyldisulfone is formed as an impurity, and contained in the mixture. Further, it has been also known that these impurities cause bad effects on thermal coloring sensitivity and storage stability of the background of the thermal recording material (Patent Document 5, Patent Document 6).

By the way, there is disclosed an invention that 4,4'-dichlorodiphenylsulfone is produced by using starting materials such as dialkyl sulfate and chlorobenzene, and reacting them for the purpose of obtaining a starting material of 4,4'-diaminodiphenyl-sulfone which becomes a curing agent of an epoxy resin. There are also disclosed that 2,4'-dichlorodiphenylsulfone is synthesized as a byproduct in the reaction, and the resulting product becomes a mixture of isomers, and further, the mixture of isomers is hydrolyzed to form a mixture of 4,4'-dihydroxydiphenylsulfone and 2,4'-dihydroxydiphenylsulfone by the two steps reaction (see Patent Document 7).

However, according to this manufacturing method, a dichlorodiphenylsulfone mixture is synthesized through the steps firstly by the reaction using the commercially available starting materials, and then hydrolysis of the resulting product to obtain a dihydroxydiphenylsulfone mixture. That is, it is necessary to undergo at least two steps of the reaction procedure of the synthesis and the hydrolysis. Therefore, the manufacturing method which undergoes the two steps of the reaction procedure has been considered to be a disadvantageous method since the manufacturing cost is clearly high as compared with the conventional manufacturing method which is to obtain a dihydroxydiphenylsulfone mixture directly by the one step of the reaction procedure from the commercially available starting materials. Accordingly, the manufacturing method of Patent Document 7 has not heretofore been considered to be a realistic method for obtaining the dihydroxydiphenylsulfone mixture.

PRIOR ART DOCUMENTS

Patent Documents

Patent Document 1: JP H5-92665A
Patent Document 2: JP 2002-120462A
Patent Document 3: JP 2002-144742A
Patent Document 4: JP 2003-246152A
Patent Document 5: JP 2004-42401A
Patent Document 6: JP 2004-114366A
Patent Document 7: GB 2476147A

SUMMARY OF THE INVENTION

Problems to be Solved by the Invention

An object of the present invention is to provide an excellent thermal recording material having both of excellent coloring property and storage stability by using 2,4'-dihydroxydiphenylsulfone with a relatively large amount, and can be obtained by a relatively simple manufacturing method with low cost.

Means to Solve the Problems

The present invention relates to a thermal recording material which comprises a support and a coloring layer containing a colorless or pale colored dye precursor and a developer provided thereon, wherein the developer contains 2,4'-dihydroxydiphenylsulfone and 4,4'-dihydroxydiphenylsulfone, and a weight ratio of the 2,4'-dihydroxydiphenylsulfone and the 4,4'-dihydroxydiphenylsulfone is within the range of exceeding 50/50 and 95/5 or less, further the 2,4'-dihydroxydiphenylsulfone and the 4,4'-dihydroxydiphenylsulfone contain materials obtained by sequentially undergoing a separating step of obtaining a second mixture where a weight ratio of 2,4'-dichlorodiphenylsulfone is heightened from a first mixture containing the 2,4'-dichlorodiphenylsulfone and 4,4'-dichlorodiphenylsulfone, a reaction step of reacting the second mixture to obtain a third mixture containing the 2,4'-dihydroxydiphenylsulfone and the 4,4'-dihydroxydiphenylsulfone, and a post-treatment step of decolorizing and purifying the third mixture. is preferred that the above-mentioned weight ratio is substantially determined by undergoing a series of the steps. It is also preferred that the above-mentioned separating step contains a crystal precipitating step. It is further preferred that the above-mentioned separating step gives a material in which a weight ratio of the 2,4'-dichlorodiphenylsulfone and the 4,4'-dichlorodiphenylsulfone is within the range of exceeding 50/50 and 95/5 or less by one separation. It is moreover preferred that the reaction of obtaining the above-mentioned third mixture is a hydrolysis reaction. It is further preferred that the reaction of obtaining the above-mentioned third mixture is a hydrolysis reaction carried out by adding an alkali. It is furthermore preferred that the above-mentioned reaction step is to obtain a third mixture by adjusting a pH after the hydrolysis reaction. It is also preferred that the above-mentioned post-treatment step is a step wherein discoloration and purification are carried out by recrystallization using a solvent.

It is also preferred that the above-mentioned coloring layer contains at least one compound, as an auxiliary agent, selected from the following (A), (B) and (C):

(A) a trisphenol type compound represented by the following formula (I):

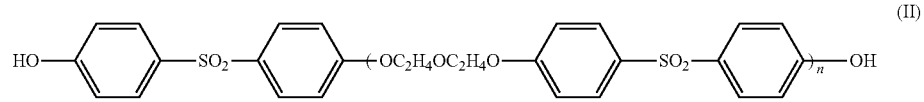

wherein $R_1$ represents an alkyl group having 4 or less carbon atoms or a cyclohexyl group, and $R_2$ represents an alkyl group having 4 or less carbon atoms.

(B) a diphenylsulfone crosslinking type compound represented by the following formula (II):

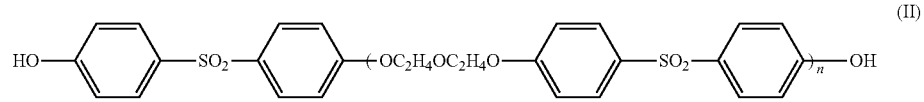

wherein n represents a numeral of 1 to 7.

(C) a urea urethane compound having a molecular weight of 2,000 or less, having both of a urea group(s) and a urethane group(s) in a molecular structure, and, aromatic compound residues are directly bonded to both ends of the respective urea group(s) and urethane group(s).

Further, it is preferred that the above-mentioned auxiliary agent (C) is a urea urethane compound represented by the following formula (III) or (IV):

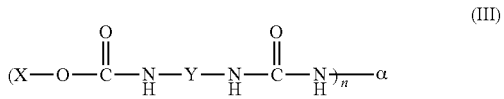

wherein X and Y each represent an aromatic compound residue, α represents an aromatic compound residue having a valence number of divalent or more, n represents an integer of 2 or more, and each residue may optionally have a substituent(s).

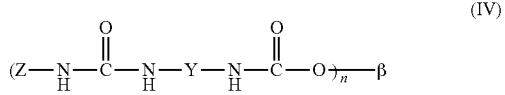

wherein Z and Y each represent an aromatic compound residue, β represents an aromatic compound residue having a valence number of divalent or more, n represents an integer of 2 or more, and each residue may optionally have a substituent(s).

It is also preferred that the above-mentioned auxiliary agent (C) is a urea urethane compound represented by the following formula (V):

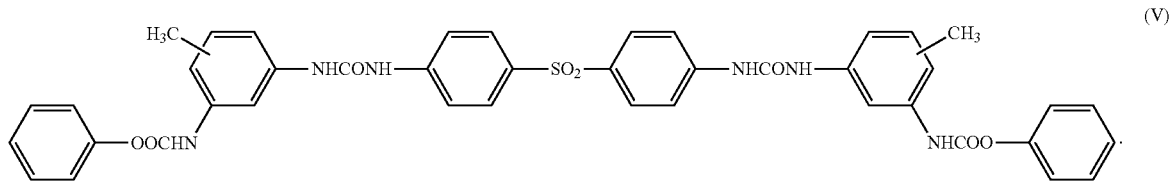

It is also preferred that the coloring layer contains at least one compound selected from diphenylsulfone, m-terphenyl, 4-benzylbiphenyl, 1,2-bis(3,4-dimethyl-phenyl)ethane, 2-benzyloxynaphthalene, 1,2-diphenoxymethylbenzene, 1,2-diphenoxyethane, 1,2-bis(3-methylphenoxy)ethane, dibenzyl oxalate, di(4-chloro-benzyl)oxalate, di(4-methyl-benzyl)oxalate, dibenzyl terephthalate, stearic acid amide and 4-acetylbiphenyl as a sensitizer.

It is further preferred that the coloring layer further contains at least one compound selected from 2,2-bis(4-hydroxyphenyl)propane, benzyl 4-hydroxybenzoate, an oligomer of hydroxybenzoate, 4-n-octyloxycarbonylaminosalicylic acid or a metal salt thereof, butyl bis(4-hydroxyphenyl)acetate, bis(3-allyl-4-hydroxyphenyl)sulfone, 4-hydroxy-4'-isopropoxydiphenylsulfone, 4-hydroxy-4'-n-propoxydiphenylsulfone, 4,4'-bis(p-toluenesulfonylaminocarbonylamino)diphenylmethane, 4-hydroxy-4'-allyloxydiphenylsulfone, N-p-toluenesulfonyl-N'-3-(p-toluenesulfonyloxy)phenylurea, 4,4'-butylidenebis(6-t-butyl-3-methylphenol) and sulfonylurea derivative as a developer.

It is moreover preferred that the coloring layer further contains at least one compound selected from 4,4'-thiobis(2-methyl-6-t-butylphenol), 4,4'-thiobis(3-methyl-6-t-butylphenol), 2,2'-thiobis(6-t-butyl-4-methylphenol), 2,2'-methylenebis(4-methyl-6-t-butylphenol), tris(2,6-dimethyl-4-t-butyl-3-hydroxybenzyl)isocyanurate, 4-benzyloxy-4'-(2-methylglycidyloxy)diphenylsulfone, 4,4'-diglycidyloxydiphenylsulfone, sodium-2,2'-methylenebis(4,6-di-t-butylphenyl)phosphate and N,N'-di-2-naphthyl-p-phenylenediamine as a preservation stabilizer.

Effects of the Invention

The thermal recording material of the present invention can be manufactured with a low cost by a relatively simple manufacturing method even when a dihydroxydiphenylsulfone mixture in which the weight ratio of the 2,4'-dihydroxydiphenylsulfone is greater than the weight ratio of the 4,4'-dihydroxydiphenylsulfone is used as the developer of the coloring layer. As a result, it is possible to provide a high performance thermal recording material with a low cost, which is excellent in coloring property including a coloring density, a thermal coloring sensitivity, and so on, and has excellent properties in image stability including disappearance of the record by a plasticizer or background fogging, and so on. More specifically, the manufacturing method as a whole becomes simpler, in spite of undergoing two steps of the processes of the separation and the reaction which are considered to be obviously high cost. When the method in the present invention is specifically compared with the conventional manufacturing method which directly manufactures the dihydroxy material, a manufacturing cost of an overall process including separation of the isomers can be reduced, since the 2,4'-dihydroxydiphenylsulfone can be formed with a relatively large amount in the first synthesis by treating through a dichloro material, and the separation process of the isomers is simple and easy so that labor and time are not so required, and so on.

Further, in the thermal recording material of the invention of the present application, more excellent properties as the thermal recording material can be obtained than the case where the material obtained by isolating the 2,4'-dihydroxydiphenylsulfone and the 4,4'-dihydroxydiphenylsulfone, and then, adding and mixing the both of them with the aimed weight ratio is used as the developer, whereas the reason is uncertain.

Moreover, phenylphenolsulfonate or trihydroxytriphenyldisulfone, which is a side reaction product inevitably generated in the conventional manufacturing method of the thermal developer, is not generated in the thermal recording material of the present invention, so that there is no decline in the performance of the thermal recording material caused by these side reaction products.

EMBODIMENTS TO CARRYOUT THE INVENTION

Figure 1:
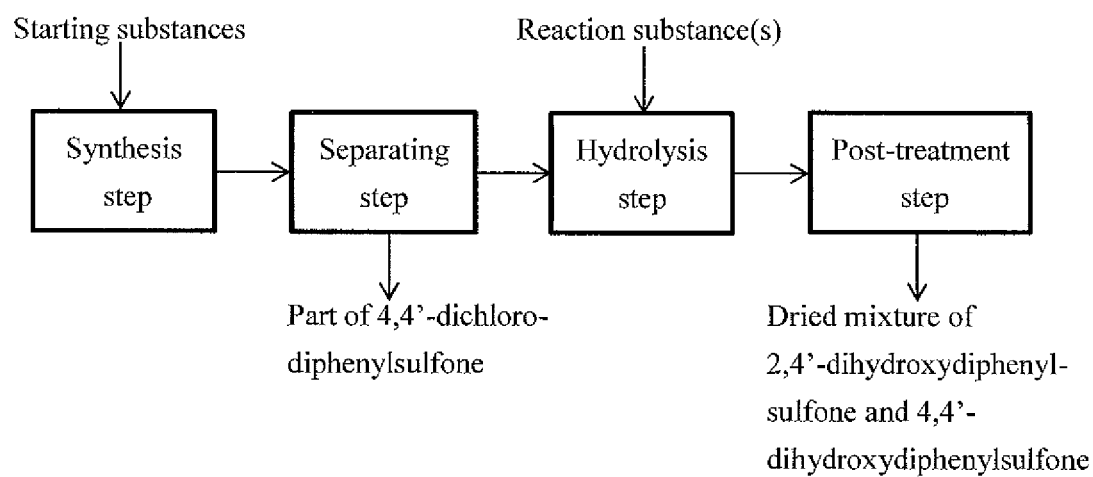
FIG. 1 is a schematic view showing outline flow of the manufacturing method of the developer to be used in the invention of the present application.
Figure 2:
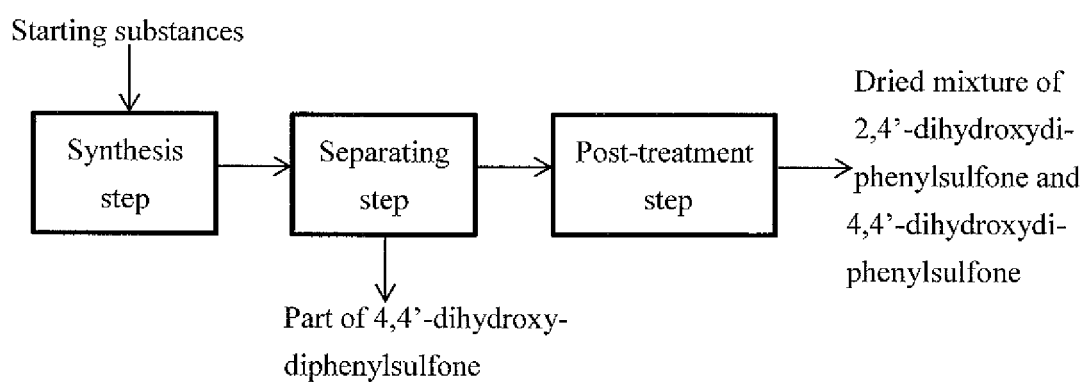
FIG. 2 is a schematic view showing outline flow of the manufacturing method of the conventional developer containing dihydroxydiphenylsulfone.

In the following, the present invention is explained more specifically by referring to the drawings. The thermal recording material of the present invention comprises a support such as paper and so on, and a coloring layer provided thereon which contains a colorless or pale colored dye precursor such as a leuco dye which is a representative example thereof, a developer which colors the dye precursor by reacting under heating, and so on.

The developer to be used in the present invention contains 2,4'-dihydroxydiphenylsulfone and 4,4'-dihydroxydiphenylsulfone, and a weight ratio of the 2,4'-dihydroxydiphenylsulfone and the 4,4'-dihydroxydiphenylsulfone is within the range of exceeding 50/50 and 95/5 or less. When the weight ratio of the two materials exceeds 50/50, a thermal recording material can be obtained which is excellent in basic properties as the thermal recording material such as thermal coloring sensitivity and so on, and which is able to ensure image stability to a certain extent. Also, the necessity of taking labor and time for isomer separation is reduced and the manufacturing cost is reduced by making the weight ratio 95/5 or less. Accordingly both of coloring property and image stability of the thermal recording material can be improved.

The mixture can be obtained by the manufacturing method mentioned below. Outline flow of the manufacturing method is shown in FIG. 1. First, a mixture of dichlorodiphenylsulfones containing 2,4'-dichlorodiphenylsulfone and 4,4'-dichlorodiphenylsulfone (hereinafter referred to as a first mixture) is synthesized by a synthesis step from the commercially available starting materials. The synthetic reaction can uses a conventionally known reaction without limitation. For example, commercially available sulfur trioxide and dimethyl sulfate are reacted to obtain a mixture of dimethyl pyrosulfate and sulfur trioxide, and the mixture may be reacted with chlorobenzene. Also, it may be employed a dehydration condensation reaction using 4-chlorobenzenesulfonic acid chloride and chlorobenzene. In these synthesis steps, 4,4'-dichlorodiphenylsulfone is generally synthesized with a ratio of about 90% by mass and 2,4'-dichlorodiphenylsulfone is generally synthesized with a ratio of about 10% by mass. That is to say, the 2,4' material is formed with a larger amount as compared with the usual case optimized for manufacturing the 4,4' material by the conventional manufacturing method for the dihydroxyphenylsulfone. Therefore, it is relatively easy to heighten the weight ratio of the 2,4' material in the subsequent treatment.

Next, a part of the 4,4'-dichlorodiphenylsulfone removed in the separation step from the first mixture obtained in the synthesis step, a second mixture is obtained in which the weight ratio of the 2,4'-dichlorodiphenylsulfone is heightened. The separating steps are, to wash the first mixture using a mixed solvent of water and an organic solvent such as monochlorobenzene and so on, then, to precipitate crystals in an organic solvent, and to separate the obtained crystals by solid-liquid separation using filtration and so on, and to remove the solvent from the obtained filtrate. According to the procedure, the second mixture can be obtained in which the weight ratio of the 2,4'-dichlorodiphenylsulfone is heightened. Separation of the dichloro isomers is relatively simple and easy since the difference of the solubilities between 2,4'-dichlorodiphenylsulfone and 4,4'-dichlorodiphenylsulfone is large, and so it is easy to obtain the second mixture in which the weight ratio of the 2,4'-dichlorodiphenylsulfone is heightened. It is preferred that removal of the 4,4'-dichlorodiphenylsulfone is so carried out by one separation that the weight ratio of the 2,4'-dichlorodiphenylsulfone and the 4,4'-dichlorodiphenylsulfone in the second mixture becomes within the range of exceeding 50/50 and 95/5 or less. However, it does not necessarily become within the range by one separation, and it is possible to become close to about 50/50. This is because that it is easy to heighten the weight ratio of the 2,4' material in the subsequent procedures. Accordingly, the separating procedure can be kept relatively simple, and the manufacturing cost of the thermal recording material can be reduced.

Next, the second mixture is reacted to obtain a third mixture containing 2,4% dihydroxydiphenylsulfone and 4,4'-dihydroxydiphenylsulfone. The synthesis reaction can uses a conventionally known reaction without limitation. For example, the second mixture is reacted in the second reaction step using a hydrolysis reaction to obtain a third mixture containing 2,4'-dihydroxydiphenylsulfone and 4,4'-dihydroxydiphenylsulfone. The hydrolysis reaction may be carried out by adding an alkali to a solvent under heating and pressure. A heating temperature is preferably from 100° C. to 300° C., more preferably from 180° C. to 250° C., further preferably from 200° C. to 240° C. The alkali to be used in the reaction is not particularly limited, and preferably sodium hydroxide, potassium hydroxide, lithium hydroxide, more preferably sodium hydroxide. The solvent to be used in the reaction is preferably water, and an organic solvent or a mixed solvent of an organic solvent and water may be used. The organic solvent can be used for the reaction may be an alkanol such as methanol, ethanol, isopropanol and so on, or an alkanol-water mixed solvent, or a chlorine-based aliphatic solvent such as dichloromethane and dichloroethane, or a chlorine-based aromatic solvent such as chlorobenzene and o-dichlorobenzene. After completion of the reaction, solid-liquid separation is carried out to remove unreacted materials and so on, further neutralizing with an acidic solution such as sulfuric acid, hydrochloric acid, and so on, to obtain crystals. It is also preferred that the obtained crystals are further subjected to dissolution, crystal precipitation and separation, and so on. More specifically, the obtained crystals are dissolved in an aqueous caustic soda solution, and a pH of the solution is properly adjusted by sulfuric acid or hydrochloric acid, and the crystals may be taken out sequentially. More preferably, precipitates in which the ratio of the 4,4' material is relatively high are generated in an alkaline pH region by the pH adjustment, so that the precipitates may be removed by filtration. Further, when the filtrate is neutralized to an acidic side, precipitates are again generated so that the precipitates may be separated by filtration. According to these procedures, the third mixture containing the 2,4'-dihydroxydiphenylsulfone and the 4,4'-dihydroxydiphenylsulfone can be obtained. Accordingly to this procedure, a part of the 4,4'-dihydroxydiphenylsulfone is removed in the form of a monosodium salt. The separating operation may be repeated with a plural number of times, but it is usually sufficient with once. This is because the separating operation is started from the point where the weight ratio of the 2,4' material is increased beforehand to the weight ratio of about 50/50 or so, for example. According to the procedure, the weight ratio of the 2,4'-dihydroxydiphenylsulfone can be further heightened, and can be adjusted within the objective weight ratio easily.

Next, a post-treatment step to decolorize and purify the third mixture is carried out. For carry out decolorization and purification, recrystallization may be carried out by using a solvent, or an activated charcoal and so on may be added to decolorize, or other decolorization method may be used. In the case of using a solvent, any solvent may be used so long as it dissolves the dihydroxydiphenylsulfone, and it may be preferably alkanols, more preferably alcohols such as methanol, ethanol, isopropanol and an alkanol-water mixed solvent. According to the procedure, it is possible to use the mixture as a developer of the thermal recording material. It is also preferred that unnecessary materials such as unreacted substance(s) and so on are removed together with the coloring component. It is also preferred to set processing conditions which can further remove a part of the 4,4'-dihydroxydiphenylsulfone during decolorization and purification, if necessary. According to the procedure, it is possible to further heighten the weight ratio of the 2,4'-dihydroxydiphenylsulfone. A drying step may be added to the post-treatment step, if necessary.

The weight ratio of the 2,4'-dihydroxydiphenylsulfone and the 4,4'-dihydroxydiphenylsulfone in the coloring layer of the thermal recording material is preferably determined substantially by undergoing the above-mentioned series of the steps. The above phrase "substantially determined" means no inclusion of the case that 2,4'-dihydroxydiphenylsulfone manufactured separately by others is added and mixed subsequently. According to the procedure, it is possible to manufacture the thermal recording material by a simple manufacturing method, and to suppress the manufacturing cost low consequently.

It is possible to add and mix subsequently the 2,4'-dihydroxydiphenylsulfone manufactured separately by others to the mixture obtained by undergoing the above-mentioned series of the steps, but there are demerits that the manufacturing method of the thermal recording material becomes complex as a whole, and the manufacturing cost becomes high. Therefore, it is more preferred that the mixture is used in the thermal recording material with the weight ratio of the isomers obtained by undergoing the above-mentioned series of the steps and contained therein as it is without undergoing such an addition and mixing step and so on.

The dihydroxydiphenylsulfone mixture thus obtained has the weight ratio of the 2,4'-dihydroxydiphenylsulfone larger than the weight ratio of the 4,4'-dihydroxydiphenylsulfone. Therefore, when it is used as a developer of the thermal recording material, a thermal recording material excellent in thermal coloring sensitivity and degree of whiteness can be obtained. Improvement can be seen also in image stability. Unfortunately, as compared with the case using a mixture in which the weight ratio of the 4,4'-dihydroxydiphenylsulfone is greater than that of the 2,4'-dihydroxydiphenylsulfone, the degree of the improvement in image stability is slightly inferior. However, a thermal recording material more excellent in image stability can be obtained by using the auxiliary agent mentioned later in the coloring layer. In addition, separation of the isomers is carried out mainly in the dichloro material having a large difference in solubility so that separation is easy. Moreover, in addition to the fact that the conditions of removing a part of the 4,4' material can also be set in the hydrolysis step or in the decolorization and purification step, if necessary, the 2,4' material is formed with a relatively large amount in the original reaction step of forming the dichloro material, so that it is relatively easy to heighten the weight ratio of the 2,4' material by removing the 4,4' material from the mixture of the isomers. Therefore, nevertheless the reaction step requires two steps of synthesis and hydrolysis, the total manufacturing method including the separating step is simple and the manufacturing cost can be reduced.

Further, the thermal recording material using the mixture is more excellent in properties as a thermal recording material than those of the thermal recording material using a developer obtained by isolating each of the 2,4'-dihydroxydiphenylsulfone and the 4,4'-dihydroxydiphenylsulfone, and drying them, and then, adding and mixing so as to become the objective weight ratio. Though the reason is uncertain, it is presumed that the both are in a well-mixed state at a molecular level when they are formed by the reaction, so that excellent properties can be obtained. This is because it is impossible to obtain a mixed state at a molecular level by isolating from each other, drying separately, and then, physically mixing. It is also possible to improve the properties by changing the weight ratio of the 2,4'-dihydroxydiphenylsulfone, if necessary, so that a thermal recording material having more excellent properties can be easily obtained.

Moreover, the mixture of the 2,4'-dihydroxydiphenylsulfone and the 4,4'-dihydroxydiphenylsulfone obtained by the reaction using the mixture containing the 2,4'-dichlorodiphenylsulfone and the 4,4'-dichlorodiphenylsulfone does not contain impurities as disclosed in Patent Documents 5, 6, and so on. From this fact, it is advantageous in its properties for obtaining a thermal recording material improved in coloring property and image stability. In addition, it is not necessary to carry out the step of removing these impurities to improve properties, so that the manufacturing cost can be reduced.

A mixed ratio of the 2,4'-dihydroxydiphenylsulfone and the 4,4'-dihydroxydiphenylsulfone when the dihydroxydiphenylsulfone mixture is used as a developer is exceeding 50/50 and 95/5 or less in a weight ratio. When the ratio exceeds 50/50, coloring property and image stability can be improved with good balance, and when the ratio is 95/5 or less, properties of the thermal recording material and the cost are well balanced. The ratio is more preferably 70/30 or more and 90/10 or less.

Further, the thermal recording material of the present invention can have both of excellent coloring property and more excellent image stability by using at least one compound selected from the following (A), (B) and (C) as an auxiliary agent in combination with the developer. That is, though the weight ratio of the 4,4'-dihydroxydiphenylsulfone is small in the developer to be used in the present invention so that storage stability tends to be insufficient, it is possible to improve the storage stability. In particular, it is more preferred to use the compound selected from the auxiliary agent (B) or (C) in combination with the developer since the material is more excellent in storage stability.

Specific examples of the trisphenol type compound represented by the above-mentioned formula (I) as the auxiliary agent (A) may be mentioned 1,1,3-tris(2-methyl-4-hydroxy-5-t-butylphenyl)butane, 1,1,3-tris(2-ethyl-4-hydroxy-5-t-butylphenyl)butane, 1,1,3-tris(2-methyl-4-hydroxy-5-cyclohexylphenyl)butane, and so on. 1,1,3-Tris(2-methyl-4-hydroxy-5-t-butylphenyl)butane can be commercially available, for example, as a trade name of ADKARKLS DH-37 (a compound wherein $R_1$ is t-butyl and $R_2$ is methyl in the formula (I), available from ADEKA Corporation). In addition, 1,1,3-tris(2-methyl-4-hydroxy-5-cyclohexylphenyl)butane can be commercially available, for example, as a trade name of ADKARKLSDH-43 (a compound wherein $R_1$ is cyclohexyl and $R_2$ is methyl in the formula (I), available from ADEKA Corporation).

The diphenylsulfone crosslinking type compound represented by the above-mentioned formula (II) as the auxiliary agent (B) may be a compound disclosed in JP Patent No. 3,913,820C or WO 97/16420A, and such a compound can be commercially available, for example, as a trade name of D-90 (available from Nippon Soda Co., Ltd.).

The urea urethane compound as the auxiliary agent (C) in which a molecular weight is 2,000 or less, having a urea group(s) and a urethane group(s) in the molecular structure, and aromatic compound residues are directly bonded to the respective both ends of the urea group(s) and the urethane group(s) is a compound disclosed in JP Patent No. 3,739,282C, JP Patent No. 3,836,867C and JP Patent No. 3,836,868C. Specific examples thereof may be exemplified by, for example, the compounds of E-1 to E-43 disclosed in JP Patent No. 3,739,282C. Among these, the compound represented by the above-mentioned formula (III) or the above-mentioned formula (IV) is preferred. Such a compound can be commercially available as a trade name of UU (a material comprising the compound represented by the formula (V) as a main component, available from Chemipro Kasei Kaisha, Ltd.).

An amount of the developer to the dye precursor to be used is not particularly limited for forming the coloring layer of the thermal recording material according to the present invention, and it is preferably used in the range of 5 to 500% by mass based on the dye precursor, and further, it is more preferably used in the range of 20 to 300% by mass. If the amount is 5% by mass or more, coloring property of the dye precursor becomes better, and it is 500% by mass or less, an excess unreacted developer is hardly remained, and it is economically preferred. Also, an amount of the auxiliary agent to the developer to be used is not particularly limited, and it is preferably used in the range of 2 to 50% by mass based on the developer, and further, it is more preferably used in the range of 5 to 40% by mass. If the amount is 2% by mass or more, improved effects on coloring property and image stability can be more clearly recognized, and the use of 50% by mass or less gives sufficient effects so that it is more preferred. Moreover, other developer, sensitizer, preservation stabilizer, dispersant, filler, lubricant, UV absorber, and so on may be used at each optional ratio, if necessary.

The leuco dye which is an example of the colorless or pale colored dye precursor to be used in the present invention is a conventionally known compound used for a pressure-sensitive recording material or a thermal recording material, and is not particularly limited. It may be mentioned, for example, the following compounds.

(1) Triarylmethane Type Compound 3,3-Bis(p-dimethylaminophenyl)-6-dimethylaminophthalide (Crystal Violet Lactone), 3,3-bis(p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl)phthalide, 3-(p-dimethylaminophenyl)-3-(2-phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-5-dimethylaminophthalide, 3,3-bis(2-phenylindol-3-yl)-5-dimethylaminophthalide, 3-p-dimethylaminophenyl-3-(1-methylpyrrol-2-yl)-6-dimethylaminophthalide, and so on.

(2) Diphenylmethane Type Compound 4,4-bis-Dimethylaminophenylbenzhydryl benzyl ether, N-halophenyl leuco auramine, N-2,4,5-trichlorophenyl leuco auramine, and so on.

(3) Xanthene Type Compound

Rhodamine B aniline lactam, rhodamine B-p-chloroanilino lactam, 3-diethylamino-7-dibenzylaminofluoran, 3-diethylamino-7-octylaminofluoran, 3-diethylamino-7-phenylfluoran, 3-diethylamino-7-chlorofluoran, 3-diethylamino-6-chloro-7-methylfluoran, 3-diethylamino-7-(3,4-dichloroanilino)fluoran, 3-diethylamino-7-(2-chloroanilino)fluoran, 3-diethylamino-6-methyl-7-anilinofluoran, 3-(N-ethyl-N-tolyl)amino-6-methyl-7-anilinofluoran, 3-piperidino-6-methyl-7-anilinofluoran, 3-(N-ethyl-N-tolyl)amino-6-methyl-7-phenethylfluoran, 3-diethylamino-7-(4-nitroanilino)-fluoran, 3-dibutylamino-6-methyl-7-anilinofluoran, 3-(N-methyl-N-propyl)amino-6-methyl-7-anilinofluoran, 3-(N-ethyl-N-isoamyl)amino-6-methyl-7-anilinofluoran, 3-(N-methyl-N-cyclohexyl)amino-6-methyl-7-anilinofluoran, 3-(N-ethyl-N-tetrahydrofuryl)-amino-6-methyl-7-anilinofluoran, 3-dipentylamino-6-methyl-7-anilinofluoran, 3-(N-ethyl-N-p-tolyl)amino-6-methyl-7-anilinofluoran, and so on.

(4) Thiazine Type Compound

Benzoyl leuco methylene blue, p-nitrobenzoyl leuco methylene blue, and so on.

(5) Spiro Type Compound

3-Methylspirodinaphthopyran, 3-ethylspirodinaphthopyran, 3,3-dichloro-spirodinaphthopyran, 3-benzylspirodinaphthopyran, 3-methylnaphtho-(3-methoxy-benzo)spiropyran, 3-propylspirobenzopyran, and so on. Also, a compound having an absorption region at near infrared and so on, such as 3,6-bis(dimethylamino)fluorene-9-spiro-3'-(6'-dimethylaminophthalide), 3-diethylamino-6-dimethylaminofluorene-9-spiro-3'-(6'-dimethylaminophthalide), 3,6-bis(diethylamino)fluorene-9-spiro-3'-(6'-dimethylaminophthalide), 3-dibutylamino-6-dimethylaminofluorene-9-spiro-3'-(6'-dimethylaminophthalide), 3-dibutylamino-6-diethylaminofluorene-9-spiro-3'-(6'-dimethylaminophthalide), 3,6-bis(dimethylamino)fluorene-9-spiro-3'-(6'-diethylaminophthalide), 3-diethylamino-6-dimethylaminofluorene-9-spiro-3'-(6'-diethylaminophthalide), 3-dibutylamino-6-dimethylaminofluorene-9-spiro-3'-(6'-diethylaminophthalide), 3,6-bis(diethylamino)fluorene-9-spiro-3'-(6'-diethylaminophthalide), 3,6-bis(dimethylamino)fluorene-9-spiro-3'-(6'-dibutylaminophthalide), 3-dibutylamino-6-diethylaminofluorene-9-spiro-3'-(6'-diethylaminophthalide), 3-diethylamino-6-dimethylaminofluorene-9-spiro-3'-(6'-dibutylaminophthalide), 3,3-bis[2-(4-dimethylaminophenyl)-2-(4-methoxyphenyl)ethenyl]-4,5,6,7-tetrachlorophthalide, and so on.

For preparing the coloring layer of the present invention, the above-mentioned colorless or pale colored dye precursor may be used one kind, or may be used two or more kinds in combination, if necessary.

A dispersant to be used for preparing the respective dispersions of the developer, the auxiliary agent or the colorless or pale colored dye precursor used in the thermal recording material of the present invention may be selected from a water-soluble polymer and a surfactant. Specific examples of these dispersants may be mentioned below.

Specific examples of the water-soluble polymer may be mentioned, for example, a synthetic polymer such as PVA, sulfonic acid-modified PVA, polyacrylamide, polymethacrylamide, polyacrylic acid, polymethacrylic acid, polyethylene oxide, polypropylene oxide, polyvinyl pyrrolidone or a copolymer thereof and so on; and a cellulose type polymer such as methyl cellulose, hydroxyethyl cellulose, hydroxypropyl cellulose, hydroxyethyl methyl cellulose, hydroxylpropyl methyl cellulose, carboxymethyl cellulose sodium salt, and so on. Among these, a PVA derivative and a cellulose derivative are preferred, and further, a modified PVA and hydroxylpropyl methyl cellulose are more preferred. Next, specific examples of the surfactant may be mentioned. The anionic surfactant may be mentioned a fatty acid salt, an alkyl sulfonic acid salt, an alkyl sulfosuccinic acid salt, an alkyl phosphoric acid salt, a polyoxyethylene alkyl sulfate salt, a polyoxyethylene alkyl allyl sulfate salt, an aromatic sulfonic acid derivative (for example, a salt of an alkyl benzenesulfonic acid, a salt of an alkyl diphenyl ether disulfonic acid, a salt of an alkyl naphthalenesulfonic acid, a salt of a naphthalenesulfonic acid formalin condensate), a polycarboxylic acid derivative (for example, a polymer or a copolymer of various kinds of carboxyl group-containing monomers, or a mixture thereof) and a polyoxyethylene alkyl phosphate ester. Also, the nonionic surfactant may be mentioned a polyoxyethylene alkyl ether, a polyoxyethylene alkyl allyl ether, an oxyethylene-oxypropylene block copolymer, a sorbitan fatty acid ester, a polyoxyethylene sorbitan fatty acid ester, a polyoxyethylene sorbitol fatty acid ester, a glycerin fatty acid ester, a polyoxyethylene fatty acid ester, a polyoxyethylene alkyl amine and an alkyl alkanolamide. Also, the amphoteric surfactant may be mentioned an alkyl betaine, an amine oxide, an imidazolinium betaine, and other, polyoxyethylene alkyl ether sulfuric acid triethanolamine, a reaction type anionic surfactant and a special polymer surfactant. Among these, the anionic surfactant is preferred, and further, the aromatic sulfonic acid derivative and the polycarboxylic acid derivative are more preferred. The aromatic sulfonic acid derivative may be more preferably mentioned a salt of a naphthalenesulfonic acid formalin condensate. These dispersant may be used alone or may be used two or more kinds in combination.

An amount of the dispersant to be used is preferably in the range of 0.5 to 50% by mass based on the colorless or pale colored dye precursor, the developer, or the auxiliary agent. It is more preferably in the range of 1 to 20% by mass.

A conventionally known optional additive(s) may be effectively used for preparing a dispersed liquid composition, if necessary. In the following, this is explained. A heat-fusible substance (sensitizer) may be contained to improve thermal coloring sensitivity of the thermal recording material of the present invention. The heat-fusible substance is preferably a material having a melting point of 60° C. to 180° C., in particular, those having a melting point of 80° C. to 140° C. are more preferred. Examples of the heat-fusible substance may be mentioned stearic acid amide, palmitic acid amide, N-methylol stearic acid amide, β-naphthylbenzyl ether, N-stearylurea, N,N'-distearylurea, β-naphthoic acid phenyl ester, 1-hydroxy-2-naphthoic acid phenyl ester, 2-(p-methylbenzyloxy)naphthalene, 2-benzyloxynaphthalene, 1,4-dimethoxynaphthalene, 1-methoxy-4-benzyloxynaphthalene, N-stearoyl urea, 4-benzylbiphenyl, 1,2-bis(3-methylphenoxy)ethane, 1,2-diphenoxyethane, 1-phenoxy-2-(4-chlorophenoxy)ethane, 1,2-bis(3,4-dimethylphenyl)ethane, 1,2-diphenoxymethylbenzene, 1,4-butanediol phenyl ether, dibenzyl terephthalate, dimethyl terephthalate, m-terphenyl, dibenzyl oxalate, di(4-chlorobenzyl)oxalate, di(4-methylbenzyl)oxalate, methyl 4-hydroxybenzoate, benzyl 4-hydroxybenzoate, (4'-chlorobenzyl) 4-hydroxybenzoate, ethyl 1,2-bis(4'-hydroxybenzoate), pentyl 1,5-bis(4'-hydroxybenzoate), hexyl 1,6-bis(4'-hydroxybenzoate), and so on. Further, 4,4'-dimethoxybenzophenone, 4,4'-dichlorobenzophenone, 4,4'-difluorobenzophenone, diphenylsulfone, 4,4'-dichlorodiphenylsulfone, 4,4'-difluorodiphenylsulfone, 4,4'-dichlorodiphenyldisulfide, diphenylamine, 2-methyl-4-methoxydiphenylamine, N,N'-diphenyl-p-phenylenediamine, 1-(N-phenylamino)naphthalene, benzyl, 1,3-diphenyl-1,3-propanedione, and so on may also be used. Among these materials, particularly preferred heat-fusible substance (sensitizer) may be mentioned stearic acid amide, diphenylsulfone, m-terphenyl, 4-benzylbiphenyl, 1,2-bis(3,4-dimethylphenyl)ethane, 2-benzyloxynaphthalene, 1,2-diphenoxymethylbenzene, 1,2-diphenoxyethane, 1,2-bis(3-methylphenoxy)ethane, dibenzyl oxalate, di(4-chlorobenzyl)oxalate, di(4-methylbenzyl)oxalate, dibenzyl terephthalate and 4-acetylbiphenyl. The above-mentioned heat-fusible substance may be used alone, or two or more in admixture. An amount thereof to be used is not limited, but it is preferably within the range of 10 to 500% by mass based on the colorless or pale colored dye precursor to obtain sufficient thermal responsibility, and further, it is more preferably within the range of 20 to 300% by mass.

Other developer(s) may be used in combination in addition to the developer used in the thermal recording material of the present invention, if necessary. The developer is an electron accepting substance generally used and is a phenol derivative, an aromatic carboxylic acid derivative or a metal salt thereof, a salicylic acid derivative or a metal salt thereof, N,N-diarylthiourea derivative, sulfonylurea derivative, and so on, and may be mentioned, for example, 2,2-bis(4-hydroxyphenyl)propane, 2,2-bis(hydroxy-phenyl)butane, 2,2-bis(hydroxyphenyl)pentane, 2,2-bis(hydroxyphenyl)heptane, 1,1-bis(4-hydroxyphenyl)cyclohexane, butyl bis(4-hydroxyphenyl)acetate, benzyl bis(4-hydroxyphenyl)acetate, bis(3-methyl-4-hydroxyphenyl)sulfone, 4-hydroxyphenyl-4'-methylphenylsulfone, 3-chloro-4-hydroxyphenyl-4'-methylphenylsulfone, 3,4-dihydroxyphenyl-4'-methylphenylsulfone, 4-isopropylphenyl-4'-hydroxyphenylsulfone, 4-hydroxy-4'-n-propoxydiphenylsulfone, 4-hydroxy-4'-isopropoxydiphenylsulfone, 4-hydroxy-4'-allyloxydiphenylsulfone, bis(3-allyl-4-hydroxyphenyl)sulfone, 4-hydroxy-phenyl-4'-benzyloxyphenylsulfone, 4-isopropylphenyl-4'-hydroxyphenylsulfone, bis(2-methyl-3-t-butyl-4-hydroxyphenyl)sulfide, methyl 4-hydroxybenzoate, benzyl p-hydroxybenzoate, an oligomer of a hydroxybenzoic acid ester, (4'-chlorobenzyl) 4-hydroxybenzoate, ethyl 1,2-bis(4'-hydroxybenzoate), pentyl 1,5-bis(4'-hydroxybenzoate), hexyl 1,6-bis(4'-hydroxybenzoate), dimethyl 3-hydroxyphthalate, stearyl gallate, lauryl gallate, methyl salicylate, ethyl salicylate, isoamyl salicylate, isopentyl salicylate, phenyl salicylate, benzyl salicylate, 4-n-octyloxysalicylic acid, 4-n-butyloxy-salicylic acid, 4-n-pentyloxysalicylic acid, 3-n-dodecyloxysalicylic acid, 3-n-octanoyl-oxysalicylic acid, 4-n-octyloxycarbonylaminosalicylic acid or a metal salt thereof, 4-n-octanoyloxycarbonylaminosalicylic acid, salicylic amide, salicylic anilide, 4,4'-butylidenebis(6-t-butyl-3-methylphenol), 4,4'-bis(p-toluenesulfonylaminocarbonyl-amino)diphenylmethane, 4,4'-bis(o-toluenesulfonylaminocarbonylamino)-diphenylmethane, 4,4'-bis(p-toluenesulfonylaminocarbonylamino)diphenylsulfide, 4,4'-bis(p-toluenesulfonylaminocarbonylamino)diphenyl ether, N-p-toluenesulfonyl-N'-3-(p-toluenesulfonyloxy)phenylurea, N-(p-toluenesulfonyl)-N'-(p-butoxycarbonyl)urea, N-(p-toluenesulfonyl)-N'-phenylurea, and so on. Among these, particularly preferred developer may be mentioned 2,2-bis(4-hydroxyphenyl)propane, benzyl 4-hydroxybenzoate, an oligomer of a hydroxybenzoic acid ester, 4-n-octyloxycarbonylaminosalicylic acid or a metal salt thereof, butyl bis(4-hydroxyphenyl)acetate, bis(3-allyl-4-hydroxyphenyl)sulfone, 4-hydroxy-4'-isopropoxydiphenylsulfone, 4-hydroxy-4'-n-propoxydiphenylsulfone, 4,4'-bis(p-toluenesulfonylaminocarbonylamino)diphenylmethane, 4-hydroxy-4'-allyloxydiphenylsulfone, N-p-toluenesulfonyl-N'-3-(p-toluenesulfonyloxy)phenylurea, 4,4'-butylidenebis(6-t-butyl-3-methylphenol), sulfonylurea derivative (trade name: PERGAFAST™-201). These optionally used developer may be used alone, or two or more in admixture. An amount thereof to be used is not limited, and is preferably within the range of 2 to 50% by mass based on the developer specified in the present application, and is more preferably within the range of 5 to 40% by mass.

For the purpose of improving background and stability of the printing, an amino compound may be added to the dispersion composition, if necessary. The amino compound which may be added is a colorless or pale colored substance having at least one primary or secondary or tertiary amino group. There may be mentioned, for example, an aniline derivative, a heterocyclic type compound, a hindered amine compound, and so on, as disclosed in WO 00/14058A.

Moreover, for the purpose of improvement of background fogging or thermal responsibility and so on, a compound may be added such as N-stearyl-N'-(2-hydroxyphenyl)urea, N-stearyl-N'-(3-hydroxyphenyl)urea, N-stearyl-N'-(4-hydroxyphenyl)urea, p-stearoyl aminophenol, o-stearoyl aminophenol, p-lauroyl aminophenol, p-butyryl aminophenol, m-acetylaminophenol, o-acetylaminophenol, p-acetylaminophenol, o-butylaminocarbonylphenol, o-stearylaminocarbonylphenol, p-stearylaminocarbonylphenol, 1,4-diglycidyloxybenzene, 4-benzyloxy-4'-(2-methylglycidyloxy)diphenylsulfone, 4,4'-diglycidyloxydiphenylsulfone, N,N'-di-2-naphthyl-p-phenylenediamine, sodium-2,2'-methylenebis(4,6-di-t-butylphenyl)phosphate, 4,4'-bis(p-toluenesulfoneamide)diphenylsulfone, 4,4'-thiobis(2-methyl-6-t-butylphenol), 4,4'-thiobis(3-methyl-6-t-butylphenol), 2,2'-thiobis(6-t-butyl-4-methylphenol), 2,2'-methylenebis(4-methyl-6-t-butylphenol), 2,2-t-methylenebis(4-ethyl-6-t-butylphenol), 2,2'-methylenebis(4,6-di-t-butylphenol), 2,2'-ethylenebis(4-methyl-6-t-butylphenol), 1,1,3-tris(3-t-butyl-4-hydroxy-6-methylphenyl)propane, 1,1,3,3-tetra(3-phenyl-4-hydroxyphenyl)propane, 1,1,3,3-tetra(3-cyclohexyl-4-hydroxy-6-methylphenyl)propane, 1,1-bis(3-t-butyl-4-hydroxy-6-methylphenyl)butane, 1,1-bis(3-cyclohexyl-4-hydroxy-6-methylphenyl)butane, tris(2,6-dimethyl-4-t-butyl-3-hydroxybenzyl)isocyanurate, and so on. Particularly preferred materials may be mentioned 4,4'-thiobis(2-methyl-6-t-butylphenol), 4,4'-thiobis(3-methyl-6-t-butylphenol), 2,2'-thiobis(6-t-butyl-4-methylphenol), 2,2'-methylenebis(4-methyl-6-t-butylphenol), tris(2,6-dimethyl-4-t-butyl-3-hydroxybenzyl)isocyanurate, 4-benzyloxy-4'-(2-methylglycidyloxy)diphenylsulfone, 4,4'-diglycidyloxydiphenylsulfone, sodium-2,2'-methylenebis(4,6-di-t-butylphenyl)phosphate, and N,N'-di-2-naphthyl-p-phenylenediamine.

The thermal recording material of the present invention comprises a thermal recording layer which can be colored by heating and is provided on a support. Specifically, a dispersion composition containing the above-mentioned developer, auxiliary agent, colorless or pale colored dye precursor such as a leuco dye, and containing additionally a heat-fusible substance(s) (sensitizer), a preservation stabilizer, and so on, if necessary, and containing further other component(s) necessary for forming the thermal recording layer, is prepared, and mixed to prepare a coating liquid. Preparation of the dispersion of each component may be carried out by finely pulverizing one or a plural kinds selected from various kinds of the compounds mentioned hereinabove in an aqueous solution containing a compound having dispersibility such as a water-soluble polymer, a surfactant, and so on, using a sand grinder and so on. A particle diameter of the dispersant in the respective dispersions of the developer, the auxiliary agent, and the colorless or pale colored dye precursor is preferably within the range of 0.1 to 10 μm, and is more preferably around 1 μm. The coating liquid is coated on a support to form a thermal recording layer.

Other components necessary for forming the thermal recording layer may be mentioned a pigment, a binder, and so on. The pigment may be mentioned, for example, diatomaceous earth, talc, kaolin, baked kaolin, calcium carbonate, magnesium carbonate, titanium oxide, zinc oxide, silicon oxide, aluminum hydroxide, urea-formalin resin, and so on. Also, a higher fatty acid metal salt such as zinc stearate, calcium stearate, and so on; waxes such as paraffin, oxidized paraffin, polyethylene, polyethylene oxide, stearic acid amide, castor wax, and so on; may be used for the purpose of preventing head abrasion, preventing sticking, and so on. In addition, a dispersant such as sodium dioctylsulfosuccinate and so on, a UV absorber such as a benzophenone type, a benzotriazole type, and so on, a discoloration inhibitor, and further a surfactant, a fluorescent dye, and so on may be contained, if necessary.

The binder may be mentioned, for example, a water-soluble binder such as starches, hydroxyethyl cellulose, methyl cellulose, carboxymethyl cellulose, gelatin, casein, polyvinyl alcohol, a modified polyvinyl alcohol, sodium polyacrylate, acrylamide/acrylic acid ester copolymer, acrylamide/acrylic acid ester/methacrylic acid terpolymer, an alkali salt of a styrene/maleic anhydride copolymer, an alkali salt of an ethylene/maleic anhydride copolymer, and so on; and a latex type water-insoluble binder such as a styrene/butadiene copolymer, a maleic acid modified propylene copolymer, an acrylonitrile/butadiene copolymer, a methyl acrylate/butadiene copolymer, and so on.

As the support of the thermal recording layer, paper is mainly used, and in addition to the paper, various kinds of woven fabric, nonwoven fabric, a synthetic resin film, laminated paper, synthetic paper, a metal foil, or a composite sheet combining these may be used depending on the purposes. The thermal recording layer may be constituted by a single layer or may be constituted by a plural number of the layers. It may be constituted by, for example, a multi-layered structure in which each coloring component is contained in the respective layers. In addition, a protective layer(s) containing a water-soluble polymer, a hydrophobic polymer, an inorganic filler, an organic filler, and so on, as a main component, which may comprise one layer, or a plural number of layers, may be provided on the thermal recording layer. Additionally, an intermediate layer containing an inorganic filler such as baked kaolin and so on, an organic filler, a polymer having a hollow structure, and so on, as a main component, which may comprise one layer or a plural number of layers, may be provided between the support and the thermal recording layer. A protective layer(s) containing a water-soluble polymer, a hydrophobic polymer, an inorganic filler, an organic filler, and so on, as a main component, which may comprise a layer or two or more layers, may be also provided under the support of the thermal recording layer. The thermal recording layer can be obtained by coating a coating liquid on a support and drying. The coating liquid can be obtained by mixing a binder and so on and each aqueous dispersion obtained by finely pulverizing the respective coloring components or other component(s). A coating amount of the coating liquid is preferably within the range of 1 to 15 $g/m^2$ in the state that the coating liquid has dried.

In the following, the present invention is more specifically explained by referring to Examples and Comparative Examples. Evaluation of the respective physical properties and preparation of the dispersion were carried out by the following methods. In the explanation, part(s) and % means parts by mass and % by mass, respectively, otherwise specifically mentioned. In addition, the weight ratio means a ratio of % by mass.

<Printing Sensitivity>

Printing was carried out on a thermal paper by using a printing tester manufactured by Ohkura Electric Co., Ltd., with a thermal head of KJT-256-8MGF1 manufactured by Kyocera Corporation, under the conditions of an applied voltage of 24V and a pulse width of 1.5 msec. A optical density of the printing was measured by a Macbeth optical densitometer RD918. The evaluation standard was described in the footnote of Table 1.

<Plasticizer Resistance>

The image colored in the same manner as mentioned above was sandwiched between transparent polyvinyl chloride sheets each having a thickness of 1 mm, and a color density of the image after allowing to stand at 45° C. for 24 hours was measured. The evaluation standard was described in the footnote of Table 1.

<Background Stability in Humidity Conditions>

Humidity resistance test was carried out by using the prepared thermal paper. The test was carried out by allowing the thermal paper to stand in an atmosphere at 40° C. and a relative humidity of 90% for 24 hours. A degree of whiteness of the non-printed part (background) was measured before and after the humidity resistance test, and an improved effect of the background stability in humidity conditions was evaluated from the changed amount. The evaluation standard was described in the footnote of Table 1.

<Preparation of Dispersion>

The mixture having the composition mentioned below was so pulverized and dispersed that an average particle diameter became 1 μm or less using a sand grinder to prepare a dispersion, whereby a dye dispersion, a developer dispersion, and an auxiliary agent dispersion were prepared.

Composition for preparing a dye dispersion:
Leuco dye: 52.5 g
5.38% aqueous solution of Goselan L3266 (trade name; available from The Nippon Synthetic Chemical Industry Co., Ltd.): 97.5 g
(A content of the leuco dye in the obtained dye dispersion is 35%)

Composition for preparing a developer dispersion:
Dihydroxydiphenylsulfone mixture: 60 g
5.38% aqueous solution of Goselan L3266 (trade name; available from The Nippon Synthetic Chemical Industry Co., Ltd.): 30 g
Distilled water: 60 g
(A content of the dihydroxydiphenylsulfone mixture in the obtained developer dispersion is 40%)

Composition for preparing an auxiliary agent dispersion:
Auxiliary agent: 60 g
5.38% aqueous solution of Goselan L3266, (trade name; available from The Nippon Synthetic Chemical Industry Co., Ltd.): 30 g
Distilled water: 60 g
(A content of the auxiliary agent in the obtained auxiliary agent dispersion is 40%)

In addition, a calcium carbonate dispersion was prepared as follows. 10 g of calcium carbonate (trade name: Callight KT, available from Shiraishi Calcium Kaisha, Ltd.) was mixed with 30 g of water and the mixture was stirred and dispersed by a magnetic stirrer to obtain a 25% calcium carbonate dispersion.

<Evaluation of Manufacturing Method>

The manufacturing method of obtaining a mixture comprising the 2,4'-dihydroxydiphenylsulfone and the 4,4'-dihydroxydiphenylsulfone which can be used as the developer of the thermal recording material was relatively evaluated with four steps based on the length of the total manufacturing method due to difficulty of the processes. Incidentally, when the commercially available dihydroxydiphenylsulfone powder was used as the starting material, the time and the number of the steps required for its manufacturing were estimated and added to the evaluation.

Example 1

Leuco dye; 35% dispersion of 3-dibutylamino-6-methyl-7-anilinofluoran (hereinafter referred to as ODB2) was prepared by the method as mentioned above.

Developer; 1 mol of dimethyl sulfate and 2 mol of sulfur trioxide were mixed and reacted, and 2 mol of chlorobenzene and a catalyst were further added to the mixture, and the resulting mixture was reacted at 30° C. for 1 hour. After the reaction, chlorobenzene was added to the resulting mixture and the mixture was stirred at 30° C. for 1 hour, and allowed to stand to separate the precipitates. 4,4'-Dichlorodiphenylsulfone was taken out by crystallization and crystal separation from the precipitates using a solvent. In the remaining filtrate, 2,4'-dichlorodiphenylsulfone and 4,4'-dichlorodiphenylsulfone were contained with a weight ratio of 65/35. Next, a dilute aqueous caustic soda solution was added to the mixture, and the resulting mixture was reacted at 220° C. under pressure for 4 hours. After cooling, unreacted dichloro compound was separated, and the mixture was treated by a dilute sulfuric acid aqueous solution, and the formed precipitates were separated by filtration, washed with water and dried to obtain a mixture of 2,4'-dihydroxydiphenylsulfone and 4,4'-dihydroxydiphenylsulfone. The obtained mixture dissolved completely in 25% aqueous caustic soda solution, a pH adjusted by adding sulfuric acid to the solution to remove a part of the 4,4'-dihydroxydiphenylsulfone as a monosodium salt, it neutralized by adding sulfuric acid further to make a pH 5.0, and the precipitates removed by filtration, a mixture of 2,4'-dihydroxydiphenylsulfone and 4,4'-dihydroxydiphenylsulfone was obtained. This was subjected to decolorization by methanol, recrystallization, purification and separation to obtain a dihydroxydiphenylsulfone mixture with a weight ratio of 70/30 (hereinafter referred to as BPS7/3). By using the resulting material, 40% dispersion was prepared by the method as mentioned above.

Evaluation of printing sensitivity and background stability in humidity conditions of the thermal paper was carried out by the following manner. The above-mentioned dispersion adjusted with a ratio so that ODB2 was 15 parts (dried material basis, hereinafter the same), BPS7/3 was 40 parts, calcium carbonate was 20 parts, further zinc stearate (trade name: Hydrin Z-7-30; available from Chukyo Yushi Co., Ltd.) was 10 parts, and further polyvinyl alcohol (trade name: Poval PVA110; available from Kuraray, Co., Ltd., was used by adjusting to a 15% aqueous solution.) was 10 parts, the mixture was stirred and mixed to obtain a coating liquid.

The coating liquid coated on a base paper having a basis weight of 50 g/m$^2$ by a bar coater, then it dried and treated by a supercalendar, a thermal paper was obtained. The coated amount at this time was 0.40 g/m$^2$ in terms of ODB2.

With regard to the thus prepared thermal paper, printing sensitivity, plasticizer resistance and background stability in humidity conditions were evaluated by the methods as mentioned above. Evaluation results were shown in Table 1.

Example 2

A thermal paper was prepared in the same manner as in Example 1 except for using a dihydroxydiphenylsulfone mixture which had been obtained by changing the conditions of the reaction, purification and separation to result a weight ratio of 2,4'-dihydroxydiphenylsulfone and 4,4'-dihydroxydiphenylsulfone of 80/20 (hereinafter referred to as BPS8/2), in place of BPS7/3 in Example 1. Printing sensitivity, plasticizer resistance and background stability in humidity conditions of the thermal paper were evaluated, and the evaluation results were shown in Table 1.

Example 3

A thermal paper was prepared in the same manner as in Example 1 except for using a dihydroxydiphenylsulfone mixture in which the weight ratio of the 2,4'-dihydroxydiphenylsulfone and the 4,4'-dihydroxydiphenylsulfone is 90/10 (hereinafter referred to as BPS9/1) in place of BPS7/3 in Example 1. Printing sensitivity, plasticizer resistance and background stability in humidity conditions of the prepared thermal paper were evaluated, and the evaluation results were shown in Table 1.

Example 4

Leuco dye; 35% dispersion of 3-dibutylamino-6-methyl-7-anilinofluoran (ODB2) was prepared by the method as mentioned above.
Developer; 40% dispersion of a dihydroxydiphenylsulfone mixture in which a weight ratio of 2,4'-dihydroxydiphenylsulfone and 4,4'-dihydroxydiphenylsulfone is 70/30 (BPS7/3) was prepared by the method as mentioned above.
Auxiliary agent; 40% dispersion of UU (trade name; available from Chemipro Kasei Kaisha, Ltd.) (hereinafter referred to as UU) was prepared by the method as mentioned above.
Evaluation of the thermal paper was carried out in the same manner as in Example 1 except for changing 40 parts of BPS7/3 in Example 1 to 30 parts of BPS7/3 and 10 parts of UU. Printing sensitivity, plasticizer resistance and background stability in humidity conditions were evaluated, and the evaluation results were shown in Table 1.

Example 5

The same procedure was done as in Example 4 except for using BPS9/1 in place of BPS7/3 in Example 4. Printing sensitivity, plasticizer resistance and background stability in humidity conditions of the prepared thermal paper were evaluated, and the evaluation results were shown in Table 1.

Example 6

A thermal paper was prepared in the same manner as in Example 4 except for using D-90 (trade name; available from Nippon Soda Co., Ltd.) in place of UU in Example 4. Printing sensitivity, plasticizer resistance and background stability in humidity conditions of the thermal paper were evaluated, and the evaluation results were shown in Table 1.

Example 7

A thermal paper was prepared in the same manner as in Example 4 except for using DH43 (trade name; available from Adeka Corporation) in place of UU in Example 4. Printing sensitivity, plasticizer resistance and background stability in humidity conditions of the thermal paper were evaluated, and the evaluation results were shown in Table 1.

Example 8

A thermal paper was prepared in the same manner as in Example 4 except for changing the amount of BPS7/3 in Example 4 to 29 parts and the amount of UU to 11 parts. Printing sensitivity, plasticizer resistance and background stability in humidity conditions of the thermal paper were evaluated, and the evaluation results were shown in Table 1.

Comparative Example 1

A thermal paper was prepared in the same manner as in Example 1 except for using a dihydroxydiphenylsulfone mixture in which a weight ratio of 2,4'-dihydroxydiphenylsulfone and 4,4'-dihydroxydiphenylsulfone is 30/70 (hereinafter referred to as BPS3/7), in place of BPS7/3 in Example 1. Printing sensitivity, plasticizer resistance and background stability in humidity conditions of the thermal paper were evaluated, and the evaluation results were shown in Table 1.

Comparative Example 2

A thermal paper was prepared in the same manner as in Example 1 except for using a powder mixture in which 2,4'-dihydroxydiphenylsulfone powder (trade name: 24BPS, available from Nicca Chemical Co., Ltd.) and 4,4'-dihydroxydiphenylsulfone powder (trade name: 44BPS, available from Nicca Chemical Co., Ltd.) are added and mixed so that a weight ratio of which became 70/30 (hereinafter referred to as 24 bps/44 bps7/3), in place of BPS7/3 in Example 1. Printing sensitivity, plasticizer resistance and background stability in humidity conditions of the thermal paper were evaluated, and the evaluation results were shown in Table 1.

Comparative Example 3

A thermal paper was prepared in the same manner as in Example 1 except for using a dihydroxydiphenylsulfone mixture in which a weight ratio of 2,4'-dihydroxydiphenylsulfone and 4,4'-dihydroxydiphenylsulfone is 20/80 (hereinafter referred to as bps2/8), which have been obtained by dehydration reaction using sulfuric acid as a sulfonating agent in a conventional manufacturing method using phenol and a sulfonating agent, in place of BPS7/3 in Example 1. Printing sensitivity, plasticizer resistance and background stability in humidity conditions of the prepared thermal paper were evaluated, and the evaluation results were shown in Table 1.

TABLE 1

| | Leuco Dye | Developer | Auxiliary agent Kind | Auxiliary agent Amount[Note 1] | Printing sensitivity[Note 2] | Plasticizer resistance[Note 3] | Background stability in humidity conditions[Note 4] | Evaluation of manufacturing method[Note 5] |
|---|---|---|---|---|---|---|---|---|
| Example 1 | ODB2 | BPS7/3 | | | ○ | ○ | ◎ | ◎ |
| Example 2 | ODB2 | BPS8/2 | | | ◎ | ○ | ◎ | ◎ |
| Example 3 | ODB2 | BPS9/1 | | | ◎ | ○ | ◎ | ◎ |
| Example 4 | ODB2 | BPS7/3 | UU | 33% | ○ | ◎ | ○ | ○ |
| Example 5 | ODB2 | BPS9/1 | UU | 33% | ◎ | ◎ | ○ | ○ |

TABLE 1-continued

|  | Leuco Dye | Developer | Auxiliary agent Kind | Amount[Note 1] | Printing sensitivity[Note 2] | Plasticizer resistance[Note 3] | Background stability in humidity conditions[Note 4] | Evaluation of manufacturing method[Note 5] |
|---|---|---|---|---|---|---|---|---|
| Example 6 | ODB2 | BPS7/3 | D-90 | 33% | ○ | ◉ | ○ | ○ |
| Example 7 | ODB2 | BPS7/3 | DH43 | 33% | ○ | ○ | ◉ | ○ |
| Example 8 | ODB2 | BPS7/3 | UU | 38% | ○ | ◉ | ○ | ○ |
| Comparative Example 1 | ODB2 | BPS3/7 |  |  | X | Δ | Δ | Δ |
| Comparative Example 2 | ODB2 | 24 bps/44 bps7/3 |  |  | Δ | ○-Δ | Δ | X |
| Comparative Example 3 | ODB2 | bps2/8 |  |  | X | ○-Δ | X | X |

Note 1)% by mass of auxiliary agent based on developer
Note 2)Optical density of image when thermal paper has been colored with printing energy of 0.51 mj/dot ◉: Density is extremely dark ○: Density is good Δ: Density is slightly low X: Density is extremely low
Note 3)Plasticizer resistance of thermal paper ◉: Color density is extremely dark ○: Color density is good Δ: Color density is slightly low X: Color density is extremely low
Note 4)Background stability in humidity conditions of thermal paper ◉: Changed amount of degree of whiteness is extremely little ○: Changed amount of degree of whiteness is a little Δ: Changed amount of degree of whiteness is slightly large X: Changed amount of degree of whiteness is extremely large
Note 5)Evaluation of manufacturing method ◉: Difficulty of processes is small and total manufacturing method is short. ○: Difficulty of processes is slightly small and total manufacturing method is slightly short. Δ: Difficulty of processes is slightly large and total manufacturing method is slightly long. X: Difficulty of processes is large and total manufacturing method is long.

UTILIZABILITY IN INDUSTRY

It can be used as a thermal recording material for various kinds of information appliances, for example, a facsimile machine, a printer and a recording equipment which employ the thermal recording system.

The invention claimed is:

1. A thermal recording material comprising:
a support and a coloring layer containing a colorless or pale colored dye precursor and a developer provided thereon, wherein the developer contains 2,4'-dihydroxydiphenylsulfone and 4,4'-dihydroxydiphenylsulfone, and
a weight ratio of the 2,4'-dihydroxydiphenylsulfone and the 4,4'-dihydroxydiphenylsulfone is within a range of exceeding 50/50 and 95/5 or less,
wherein the 2,4'-dihydroxydiphenylsulfone and the 4,4'-dihydroxydiphenylsulfone comprises 2,4'-dihydroxydiphenylsulfone and 4,4'-dihydroxydiphenylsulfone obtained by sequentially undergoing:
a separating step of obtaining a second mixture where a weight ratio of 2,4'-dichlorodiphenylsulfone is heightened from a first mixture containing the 2,4'-dichlorodiphenylsulfone and 4,4'-dichlorodiphenylsulfone,
a reaction step of reacting the second mixture to obtain a third mixture containing the 2,4'-dihydroxydiphenylsulfone and the 4,4'-dihydroxydiphenylsulfone, and
a post-treatment step of decolorizing and purifying the third mixture.

2. The thermal recording material according to claim 1, wherein the weight ratio is substantially determined by undergoing a series of the steps.

3. The thermal recording material according to claim 1, wherein the separating step contains a crystal precipitating step.

4. The thermal recording material according to claim 1, wherein the separating step gives a material in which a weight ratio of the 2,4'-dichlorodiphenylsulfone and the 4,4% dichlorodiphenylsulfone is within a range of exceeding 50/50 and 95/5 or less by one separation.

5. The thermal recording material according to claim 1, wherein the reaction of obtaining the third mixture is a hydrolysis reaction.

6. The thermal recording material according to claim 1, wherein the reaction of obtaining the third mixture is a hydrolysis reaction carried out by adding an alkali.

7. The thermal recording material according to claim 1, wherein the reaction step is to obtain a third mixture by adjusting a pH after the hydrolysis reaction.

8. The thermal recording material according to claim 1, wherein the post-treatment step is a step wherein discoloration and purification are carried out by recrystallization using a solvent.

9. The thermal recording material according to claim 1, wherein the coloring layer further contains at least one compound, as an auxiliary agent, selected from the following (A), (B) and (C):

(A) a trisphenol type compound represented by the following formula (I):

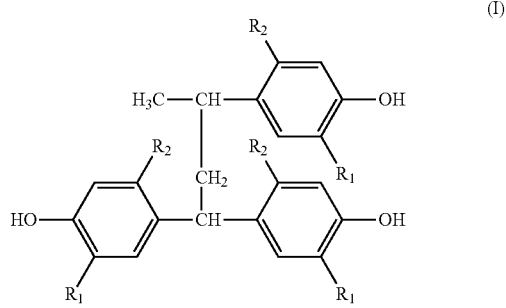

(I)

wherein $R_1$ represents an alkyl group having 4 or less carbon atoms or a cyclohexyl group, and $R_2$ represents an alkyl group having 4 or less carbon atoms, (B) a diphenylsulfone crosslinking type compound represented by the following formula (II):

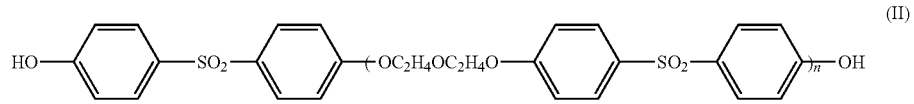

wherein n represents a numeral of 1 to 7, (C) a urea urethane compound having a molecular weight of 2,000 or less, having both of a urea group(s) and a urethane group(s) in a molecular structure, and aromatic compound residues are directly bonded to both ends of the respective urea group(s) and urethane group(s).

10. The thermal recording material according to claim 9, wherein the (C) is a urea urethane compound represented by the following formula (III) or (IV):

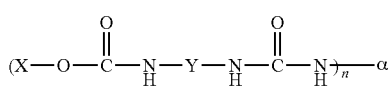

wherein X and Y each represent an aromatic compound residue, α represents an aromatic compound residue having a valence number of divalent or more, n represents an integer of 2 or more, and each residue may optionally have a substituent(s)

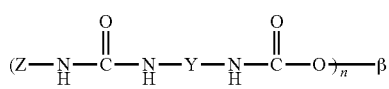

wherein Z and Y each represent an aromatic compound residue, β represents an aromatic compound residue having a valence number of divalent or more, n represents an integer of 2 or more, and each residue may optionally have a substituent(s).

11. The thermal recording material according to claim 9, wherein the (C) is a urea urethane compound represented by the following formula (V):

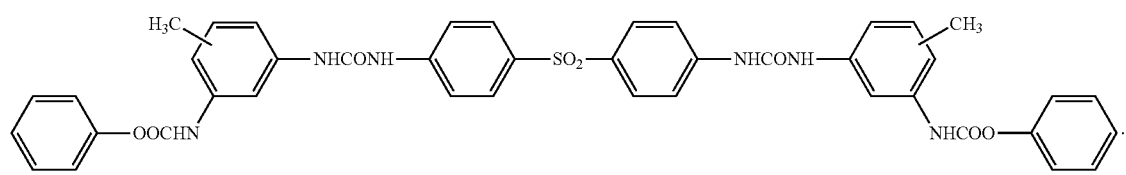

12. The thermal recording material according to claim 9, wherein the coloring layer contains at least one compound selected from diphenylsulfone, m-terphenyl, 4-benzylbiphenyl, 1,2-bis(3,4-dimethylphenyl)ethane, 2-benzyloxynaphthalene, 1,2-diphenoxymethylbenzene, 1,2-diphenoxyethane, 1,2-bis(3-methylphenoxy)ethane, dibenzyl oxalate, di(4-chlorobenzyl) oxalate, di(4-methylbenzyl) oxalate, dibenzyl terephthalate, stearic acid amide and 4-acetylbiphenyl as a sensitizer.

13. The thermal recording material according to claim 9, wherein the coloring layer further contains at least one compound selected from 2,2-bis(4-hydroxyphenyl)propane, benzyl 4-hydroxybenzoate, an oligomer of hydroxybenzoate, 4-n-octyloxycarbonylaminosalicylic acid or a metal salt thereof, butyl bis(4-hydroxyphenyl)acetate, bis(3-allyl-4-hydroxyphenyl)sulfone,4-hydroxy-4'-isopropoxydiphenylsulfone,4-hydroxy-4'-n-propoxydiphenylsulfone,4,4'-bis(p-toluenesulfonylaminocarbonylamino)diphenylmethane, 4-hydroxy-4'-allyloxydiphenylsulfone,N-p-toluenesuifonyl-N'-3-(p-toluenesulfonyloxy)phenylurea, 4,4'-butylidenebis(6-t-butyl-3-methylphenol) and sulfonylurea derivative, as a developer.

14. The thermal recording material according to claim 9, wherein the coloring layer further contains at least one compound selected from 4,4'-thiobis(2-methyl-6-t-butylphenol), 4,4'-thiobis(3-methyl-6-t-butylphenol), 2,2'-thiobis(6-t-butyl-4-methylphenol), 2,2'-methylenebis(4-methyl-6-t-butylphenol), tris(2,6-dimethyl-4-t-butyl-3-hydroxybenzyl)isocyanurate, 4-benzyloxy-4'-(2-methylglycidyloxy)diphenylsulfone,4,4'-diglycidyloxydiphenylsulfone, sodium-2,2'-methylenebis(4,6-di-t-butylphenyl)phosphate and N,N'-di-2-naphthyl-p-phenylenediamine as a preservation stabilizer.

15. The thermal recording material according to claim 1, wherein the coloring layer contains at least one compound selected from diphenylsulfone, m-terphenyl, 4-benzylbiphenyl, 1,2-bis(3,4-dimethylphenyl)ethane, 2-benzyloxynaphthalene, 1,2-diphenoxymethylbenzene, 1,2-diphenoxyethane, 1,2-bis(3-methylphenoxy)ethane, dibenzyl oxalate, di(4-chlorobenzyl) oxalate, di(4-methylbenzyl) oxalate, dibenzyl terephthalate, stearic acid amide and 4-acetylbiphenyl as a sensitizer.

16. The thermal recording material according to claim 1, wherein the coloring layer further contains at least one compound selected from 2,2-bis(4-hydroxyphenyl)propane, benzyl 4-hydroxybenzoate, an oligomer of hydroxybenzoate, 4-n-octyloxycarbonylaminosalicylic acid or a metal salt thereof, butyl bis(4-hydroxyphenyl)acetate, bis(3-allyl-4-hydroxyphenyl)sulfone,4-hydroxy-4'-isopropoxydiphenylsulfone,4-hydroxy-4'-n-propoxydiphenylsulfone,4,4'-bis(p-toluenesulfonylaminocarbonylamino)diphenylmethane, 4-hydroxy-4'-allyloxydiphenylsulfone,N-p-toluenesulfonyl-N'-3-(p-toluenesulfonyloxy)phenylurea, 4,4'-butylidenebis(6-t-butyl-3-methylphenol) and sulfonylurea derivative, as a developer.

17. The thermal recording material according to claim 1, wherein the coloring layer further contains at least one compound selected from 4,4'-thiobis(2-methyl-6-t-butylphenol), 4,4'-thiobis(3-methyl-6-t-butylphenol), 2,2'-thiobis(6-t-butyl-4-methylphenol), 2,2'-methylenebis(4-methyl-6-t-butylphenol), tris(2,6-dimethyl-4-t-butyl-3- hydroxybenzyl)isocyanurate, 4-benzyloxy-4'-(2-methylglycidyloxy)diphenylsulfone,4,4'-diglycidyloxydiphenylsulfone,sodium-2,2'-methylenebis(4,6-di-t-butylphenyl)phosphate and N,N'-di-2-naphthyl-p-phenylenediamine as a preservation stabilizer.

* * * * *